United States Patent
Andersson et al.

(10) Patent No.: US 9,610,220 B2
(45) Date of Patent: Apr. 4, 2017

(54) CYLINDRICAL COLLAPSIBLE CONTAINER

(71) Applicant: DENTSPLY International Inc., York, PA (US)

(72) Inventors: Fredrik Andersson, Göteborg (SE); Marie-Josée Michon-Gente, Göteborg (SE)

(*) Notice: Subject to any disclaimer, the term of this patent is extended or adjusted under 35 U.S.C. 154(b) by 33 days.

(21) Appl. No.: 14/662,314

(22) Filed: Mar. 19, 2015

(65) Prior Publication Data

US 2015/0335529 A1    Nov. 26, 2015

Related U.S. Application Data

(63) Continuation of application No. 14/538,059, filed on Nov. 11, 2014, now abandoned, which is a (Continued)

(30) Foreign Application Priority Data

Jun. 3, 2013    (EP) .................................... 13170288

(51) Int. Cl.
   *B65D 6/00*      (2006.01)
   *A61J 1/14*      (2006.01)
   *A61M 3/02*      (2006.01)

(52) U.S. Cl.
   CPC .......... *A61J 1/1475* (2013.01); *A61M 3/0233* (2013.01); *A61M 3/0245* (2013.01); *A61M 3/0258* (2013.01); *Y10T 29/49002* (2015.01)

(58) Field of Classification Search
   CPC ..... B65D 1/0292; B65D 11/18; Y10S 215/90; Y10S 297/08
   (Continued)

(56) References Cited

U.S. PATENT DOCUMENTS 1,647,210 A    11/1927    Bryans
3,557,788 A    1/1971    Swartz
(Continued)

FOREIGN PATENT DOCUMENTS

EP    1591369 A1    11/2005
GB    586687 A    3/1947
(Continued)

OTHER PUBLICATIONS

European search report, Application No. 13170288.8, Dated Oct. 3, 2013.

*Primary Examiner* — Shawn M Braden
(74) *Attorney, Agent, or Firm* — McNees Wallace & Nurick LLC

(57) ABSTRACT

There is provided a container (1) for medical use forming a closed compartment (17) for carrying a liquid. The container (1) comprises a flexible side wall (5), a rigid top portion (4) and a rigid bottom portion (3). In the top portion (4) there is at least one through-hole. The side wall (5), the top (4) and bottom (3) portions together form a compartment (17). Inside the compartment (17), a flexible tube (5) is arranged with one end (21) in fluid communication with a though-hole (12) in the top portion (4). A second end (19) of the tube is connected to the bottom portion (3) via a snap-in connection (18). Liquid from the inside of the container (1) may be withdrawn by pressurizing the compartment (17) in which liquid is stored, when in use. The container (1) is reversible folded and unfolded for convenient filling and storing of the container (1). The container (1) is adapted for use in an irrigation system, and preferably a system for rectal irrigation.

12 Claims, 5 Drawing Sheets

Related U.S. Application Data continuation of application No. 14/537,195, filed on Nov. 10, 2014, now abandoned, which is a continuation of application No. 14/293,336, filed on Jun. 2, 2014, now abandoned.

(58) Field of Classification Search
   USPC .................................................... 220/666
   See application file for complete search history.

(56) References Cited

U.S. PATENT DOCUMENTS

| | | | |
|---|---|---|---|
| 3,641,999 A | 2/1972 | Greene | |
| 3,946,903 A * | 3/1976 | Parker | B29C 49/48 |
| | | | 215/900 |
| 4,592,492 A | 6/1986 | Tidmore | |
| 4,607,755 A * | 8/1986 | Andreozzi | A47G 19/2266 |
| | | | 215/229 |
| 5,615,791 A | 4/1997 | Vatelot et al. | |
| 7,942,578 B2 | 5/2011 | Andersen | |
| 8,091,741 B2 * | 1/2012 | Pritchard | B05B 11/0043 |
| | | | 222/189.1 |
| 9,238,520 B2 * | 1/2016 | Jeremiah | B65D 1/0292 |
| 2009/0218357 A1 * | 9/2009 | Byrd | A47G 19/2272 |
| | | | 220/592.2 |
| 2010/0174252 A1 | 7/2010 | Tanghoej et al. | |

FOREIGN PATENT DOCUMENTS

| | | |
|---|---|---|
| WO | 03030968 A1 | 4/2003 |
| WO | 03030969 A1 | 4/2003 |
| WO | 2008087220 A1 | 7/2008 |
| WO | 2009092380 A1 | 7/2009 |
| WO | 2011023196 A1 | 3/2011 |

* cited by examiner

CYLINDRICAL COLLAPSIBLE CONTAINER

REFERENCE TO RELATED APPLICATIONS

This application is a continuation of U.S. patent application Ser. No. 14/538,059, filed Nov. 11, 2014 and entitled "Cylindrical Collapsible Container", now abandoned, which is a continuation of U.S. patent application Ser. No. 14/537,195, filed Nov. 10, 2014 and entitled "Cylindrical Collapsible Container", now abandoned, which is a continuation of U.S. patent application Ser. No. 14/293,336, filed Jun. 2, 2014 and entitled "Cylindrical Collapsible Container", now abandoned, which claims priority to EP13170288.8, filed Jun. 3, 2013 and entitled "Cylindrical Collapsible Container".

TECHNICAL FIELD

The present invention relates to a container for holding a liquid. In particular the invention is related to such a container for medical use, such as a container for use in irrigation, e.g. rectal or urinary irrigation, or supply of liquid in other types of medical applications, for treatment of a human or animal patient. The container is particularly useable for rectal irrigation, and is suitable for self-administration of an irrigation liquid.

BACKGROUND OF THE INVENTION

Containers for storing, collecting or transporting liquids are widely used in e.g. the food industry or in the medical field. In the medical field, containers are frequently used for e.g. collecting or storing of body liquids or liquid medications but also for delivery of a liquid to a patient. Such a delivered liquid may be for e.g. intravenous, flushing, or rectal enema. A liquid to be delivered to a patient may also be known as an irrigation liquid.

Administrating an irrigation liquid is a common medical procedure whereby liquid is injected into a bodily cavity, such as into the rectum and lower intestine of a patient in order to induce bowel movement. The need for such a procedure typically arises in patients suffering from certain physical ailments in which voluntary bowel control is impaired or when the bowel needs to be cleaned before e.g. a coloscopy or a surgical operation. To this end, irrigation systems may be used e.g. by people suffering from spinal cord injuries, spina bifida or multiple sclerosis. For such users, irrigation may improve quality of life by preventing constipation, reducing time spent for bowel emptying procedures, reducing fecal incontinence, and by increasing independency in general.

Irrigation is nowadays often performed outside medical attendance premises, such as in the patient's home, and is also often performed by the patient himself, i.e. by self-administration. Hereby, the patient need to do multiple tasks at the same time, or immediately following on each other, such as inserting the probe in a correct position, adequately fixating the probe in the bodily cavity, enabling the liquid to be discharged for irrigation and discharge a correct dose of irrigation liquid, and removing the probe after use. Further, many of the users of irrigation systems have reduced dexterity, which makes the operation even more cumbersome.

It is further of importance that the irrigation system is of a limited size, and portable. Portability of the irrigation system is important to disabled persons who are not hospitalised or bed-ridden if they are to live as normal a life as possible. This is particularly important if they travel away from their home, for instance, to someone else's home or if they stay in a hotel. In this situation, they need to be able to deal with their bowel function easily.

Various irrigation systems are known in the art, such as is disclosed in WO 2008/087220, WO 2009/092380, WO 03/030969, WO 2011/023196 and WO 03/030968. However, despite the attempts to make these devices user friendly, all of these irrigation devices are still relatively large and complicated to use, especially for self-administration of the irrigation liquid, and also, most of these known devices are made of many different components and are relatively costly to produce.

For delivery of irrigation liquid stored in a container a certain pressure is often required in the container to enable a flow of liquid from the container. In some cases the container, for example for intravenous insertion, is hanged above the patient. In other cases the container is pressurized by external means such as physical deformation of the container or by pumping of air into the container.

In many cases it is desirable that the container may be collapsible in order to save space before and after usage. In particular, this is desirable when storing the container prior to use or when transporting containers to a user.

In US 2010/0174252 a container for rectal irrigation is disclosed. The disclosed container relies on air to be pumped into the reservoir in order to provide sufficient pressure for delivery of liquid.

U.S. Pat. No. 3,641,999 discloses another container for use as an irrigation liquid reservoir. It is arranged such that it may stand up on a rigid bottom portion and it has an outlet tube at the bottom portion. The container as disclosed in U.S. Pat. No. 3,641,999 is collapsible.

Another container to be used for irrigation is disclosed in U.S. Pat. No. 7,942,578. It is a collapsible container comprising seams for holding the container together. A hole is arranged for adding or withdrawing liquid form the container.

The known collapsible containers suffer from a number of drawbacks. For example, it would be desirable to allow a space efficient storage of the container without compromising the stability of the container, while allowing the container to be in a standing-up configuration when in use. Furthermore, it is desirable to allow an efficient withdrawal of the entire volume of liquid contained in the container, without leaving unnecessary residues when in use. It is also desirable to reduce the risk of continuing pumping when the container is empty, or almost empty. It is further desirable to facilitate handling of the container, such as filling of liquid into the container, for users having reduced dexterity. It is also desirable to have a container which is reusable, and which may easily be emptied, dried and compacted between uses. Still further, there is a need for containers of this type which can be made relatively cost-efficiently.

Thus, there is a need for an improved collapsible container, in particular for medical use, such as for holding and delivering of irrigation liquid.

SUMMARY OF THE INVENTION

In view of the above mentioned need, a general object of the present invention is to provide an improved container for holding e.g. irrigation liquid which at least to some extent alleviates the above-discussed problems of the prior art, and at least partly fulfils the above-discussed needs.

This object is achieved by means of a collapsible container and a method for reversably compacting a container in accordance with the appended claims.

According to a first aspect of the present invention, there is provided an apparatus comprising a container for medical use forming a closed compartment for carrying a liquid, comprising: a side wall member formed by a sheet material and forming a side wall of the closed compartment, the side wall member comprising oppositely arranged first and second open ends; a rigid bottom portion arranged at the first open end of the side wall member such that the bottom portion seals the first open end of the side wall member, thereby forming a bottom of the closed compartment; a rigid top portion arranged at the second open end of the side wall member such that the top portion seals the second open end of the side wall member, the top portion forming the top of the container, and having at least a first through going hole; and a flexible tube arranged inside the compartment, the tube having a first end portion and a second end portion; wherein, the first end portion of the tube is connected to the bottom portion, the first end portion being provided with an opening towards the compartment, and the second end portion is connected to the top portion and in fluid communication with the first hole of the rigid top portion; wherein the side wall member is flexible such that the container is reversibly foldable and unfoldable, thereby being arrangeable in a compact state, in which the rigid top and bottom portions are arranged relatively closer to each other, and in an expanded state, in which the rigid top and bottom portions are arranged relatively further apart, respectively.

The seal between the side wall member and the top and bottom portions, respectively, are preferably arranged as a fixed connection, e.g. obtainable by means of welding, adhesion or the like. However, reversible connections are also feasible.

The term "rigid" here indicates that the top and bottom portions are more rigid, and preferably substantially more rigid, than the side wall member. Preferably, the top and bottom portions maintain their shape during normal use.

The present invention is based on the realization that by arranging a collapsible wall between relatively rigid bottom and top portions, a very stable container is obtained, which may still be highly compressible. Further, the arrangement of an internal tube, connecting an outlet/inlet at the bottom to the top, the container becomes easy and reliable to drain/fill. This compressible container has several further advantages over prior art containers. A compressible container is easy to fill because the size of the container is relatively compact, with an efficient space utilization, and also the shape may easily be adapted to e.g. different sized sinks. The container is also easy to fill in situations where a tap or filling station is at a different angle. In such case, the container may be appropriately flexed at the compressible side walls.

The container is further advantageous because the container may be very compact in the compacted disposition. This way, storing and transporting of the container, or a plurality of containers may be more efficient. In particular, the container may, in the compacted state, be relatively flat and disk shaped, which makes the container easy to carry around, e.g. in a pocket or a bag.

The rigid top and bottom portions makes the container have a high stability while having the flexible side walls. This is advantageous because it may allow e.g. a stable up-right position of the container when in use.

A flexible tube is advantageously connected at the bottom portion. This way, the container may more efficiently be emptied during use. Furthermore, it may prevent pumping air or the like out from the container since the opening of the tube inside the container is ensured to stay close to the bottom, and below a level of liquid in the container.

The container may be produced in a cost-efficient way. The container is further reusable and easy to clean, dry and compact after use.

According to an embodiment of the present invention, a second through going hole is arranged such that, when in use, liquid may pass through the tube and the first hole through a sealed connection between the tube and the top portion, and such that if pressurized gas is supplied through the second hole, when in use, liquid from inside the enclosure will be provided through the tube and through the first hole. This is advantageous because it allows a user-friendly way to withdraw liquid from inside the container. The second hole may be arranged such that it allows pressurized air to enter at the top portion such that it may pressurize the inside of the container. This way, liquid may be forced out from the container through the tube and the first hole.

The flexible tube is advantageously twisted, to curl up when the container is brought to the compact state. This is advantageous because it facilitates compacting of the container. This way, the flexible tube may be curled up into a compact state when the container is compressed into a compacted state. By the term "twisted" is here preferably meant that the first end portion and the second end portion of the tube are relatively rotated with respect to each other in comparison with a normal, unbiased state.

Further, the container may comprise at least one locking element to maintain the container in the compact state. This is advantageous because it may prevent the container from unfolding into a state different from a compacted state. This way, the container may be stored in a compacted state with reduced risk of unfolding to an expanded state. A locking member may be a pivotally arranged snap in connection. Such locking elements may also be realized as a stretchable or un-stretchable band movable around the container, by hooks, or the like.

The present invention may further comprises a handle in the top portion. A handle may be pivotally arranged such that it may be folded towards the top portion. This way, the overall size of the container may be reduced. A handle is advantageous because it may enable easier transportation of the container by a user. A handle may allow a user to move the container in a more user-friendly way. A handle may allow a user to hang the container from an appropriate element.

Similarly, the present invention further comprises a handle in the bottom portion. A handle may be pivotally arranged such that it may be folded towards the bottom portion. This way, the overall size of the container may be reduced. A handle is advantageous because it may enable easier transportation of the container by a user. A handle may allow a user to move the container in a more user-friendly way. A handle may allow a user to hang the container from an appropriate element. This is e.g. useable for drying the container after use.

According to an embodiment of the present invention, in the compact state, the top and bottoms portions are in contact with each other. This way, the size of the container is efficiently reduced for e.g. storage, filling, or transportation. Contact may be made at one or several contact points. At contact the top and bottom portions may be essentially parallel to each other. Hereby, the height of the container in the compact state will essentially correspond to the height of the top and bottom portions.

The top and bottom portions are preferably essentially equal in diameter and circumferential shape. This allows the side wall member to be shaped as a tube with even diameter. However, the top and bottom portions may also have different dimensions and/or shapes. Hereby, one of the top and bottom portions may e.g. be allowed to be at least partly accommodated by the other in the collapsed state.

Furthermore, in the compact state, the top and bottoms portions may be rotated relative each other compared to when in the expanded state. This is advantageous because it may allow the size of the container to be further reduced when in the compacted state. This, way the flexible side walls may collapse in a direction essentially perpendicular to a longitudinal direction of the container. In other words, in a direction essentially perpendicular to the direction the container may be compacted. This way, the side walls may collapse in both the longitudinal direction and in a transverse direction. However, collapsing solely in the longitudinal direction is also possible.

In the compact state, the container may be less than the height of the expanded state, and preferably less than ⅓, and more preferably less than ¼, and even more preferred less than ⅕. This is advantageous because it may allow more size efficient storage or transportation of the container. It may further allow filling of the container from taps or filling stations with reduced or cramped space. Preferably, the height of the container in the collapsed state is less than 5 cm, and most preferably less than 3 cm for a container capable of holding at least 1 liter in the expanded state.

Preferably, the side wall member is cylindrical in the expanded state. This way, the container may be easy to produce. Furthermore, it may facilitate compacting of the container.

The flexible side wall may be formed in various ways. It may e.g. be produced as a tubular member by means of extrusion or injection molding. It may also be formed by one or several sheet materials, e.g. connected together by means of welding or adhesion. However, other production methods may also be used, such as vacuum forming and the like.

According to an embodiment of the present invention, the container is advantageously adapted for use in an irrigation system, and preferably a system for rectal irrigation.

The tube is advantageously made from silicone. This is advantageous because it may facilitate production of the container. It may also make production cost efficient. It is further advantageous because silicone is a strong and flexible material. However, other materials may also be used.

According to an embodiment of the present invention, the top portion comprises a lid pivotally connected to the top portion and arranged to cover and seal a filling hole. This is advantageous because it may prevent unintentional spilling of liquid from inside the container. The lid may advantageously be attached to the top portion with a snap-in connection. When the container is in use, the lid may seal the filling hole of the container. There may advantageously be an o ring arranged between the filling hole and the lid.

The lid arranged on the top portion may further comprise a pressure valve arranged and configured to hold a pressure of at least 150 mbar inside the container, but release pressure when a certain threshold level has been obtained. This is advantageous because it may protect the container from overpressure. For example, the flexible tube may be clogged or otherwise prevented from allowing liquid to be withdrawn from the container when pressurized air is applied to the inside of the container. In such case, the pressure valve may prevent disruption of the container due to overpressure.

Moreover, the tube is attached to the bottom portion via a snap-in connection. This may advantageously keep the second end of the flexible tube connected at the bottom portion. A snap-in connection may be easy to fabricate and it may allow a user-friendly reversible attachment of the tube to the bottom portion.

The container may advantageously comprise a temperature sensor for sensing a temperature of the liquid. This is advantageous because it may allow a direct read-out of the temperature of the liquid before use. The temperature of the liquid may be important for some applications, or it may be important for comfort for a user.

Preferably, the side wall member is made from a plastic material, such as polypropylene, polyimide, polyethylene, EBA, or combinations thereof. This is advantageous because it may facilitate production of the container. It may also make production cost-efficient. It is advantageous because the above-mentioned materials are flexible materials. However, other materials are also useable.

According to another aspect of the invention, there is provided an irrigation system, comprising a collapsible container of the above-discussed type. The irrigation system is preferably a portable system, and preferably a system intended for self-administration. In addition to the container, serving as a reservoir for housing the irrigation liquid, the system may in addition comprise all, or at least some of the following additional elements:
  a probe for arrangement in a user;
  A pump for directly or indirectly pumping irrigation liquid from the reservoir/container to the probe;
  a control unit for controlling the pump, and thereby also the transfer of said irrigation liquid; and
  tubing providing fluid communication between said reservoir, control unit and probe.

According to a further aspect of the invention, there is provided a method for reversibly compacting a container, comprising the steps of: moving a rigid bottom portion and a rigid top portion of the container towards each other, thereby collapsing a side wall member formed by a flexible material arranged between the rigid bottom and top portions; and locking the rigid bottom and top portions to each other in the compacted state; wherein the container further comprises a flexible tube arranged inside the compartment, the tube being connected to the bottom portion and the top portion to provide fluid communication between the interior bottom of the container and a discharge hole of the rigid top portion; wherein, the tube and the side wall member are reversibly foldable and unfoldable.

By means of these further aspects, similar advantages and advantageous embodiments as discussed above in relation to the first aspect are obtainable.

According to an embodiment, moving the top and bottom portions away from each other comprises rotating the top and bottom portions relative to each other. This is advantageous because it may allow the size of the container to be further reduced when in the compacted state. This, way the flexible side walls may collapse in a direction essentially perpendicular to a longitudinal direction of the container. In other words, in a direction essentially perpendicular to the direction the container may be compacted. It is further advantageous because it may allow collapsing the container in a more controlled way since the side wall is compacted more efficiently.

BRIEF DESCRIPTION OF THE DRAWINGS

For exemplifying purposes, the invention will be described in closer detail in the following with reference to embodiments thereof illustrated in the attached drawings, wherein.

DETAILED DESCRIPTION OF PREFERRED EMBODIMENTS

Figure 1:
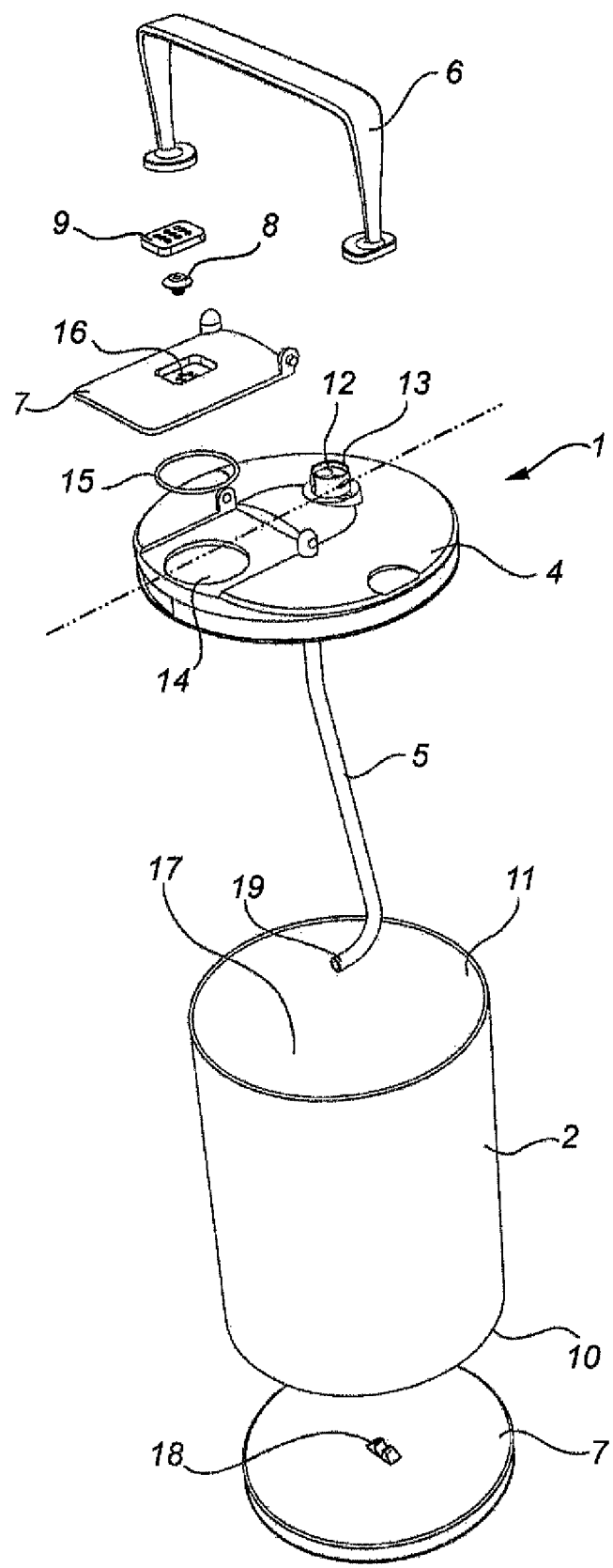
FIG. 1 is an exploded view of a container according to an embodiment of the present invention.

The present invention will now be described more fully hereinafter with reference to the accompanying drawings, in which a currently preferred embodiment of the invention is shown. This invention may, however, be embodied in many different forms and should not be construed as limited to the embodiments set forth herein; rather, these embodiments are provided for thoroughness and completeness, and fully convey the scope of the invention to the skilled addressee. Like reference characters refer to like elements throughout. The illustrated embodiment is shown with reference to be used in an irrigation system, and preferably a system for rectal irrigation.

The apparatus illustrated in the exploded view FIG. 1 comprises a container 1 which comprises a side wall member 2, a rigid bottom portion 3, a rigid top portion 4, a flexible tube 5, a handle 6, a first lid 7, a pressure valve 8, and a second lid 9.

In the embodiment illustrated in FIG. 1, when assembled, the bottom portion 3 is arranged at a first open end 10 of the side wall member 2 such that it seals the first open end 10. The rigid top portion 4 is arranged at a second open end 11 of the side wall member 2 such that it seals the second open end. There are a first 12, a second 13 and a third 14 through-hole in the rigid top portion 4. The third through hole being a filling hole 14, may be used for filling the container 1 with a liquid, has an o-ring 15 arranged around the circumference of the hole 14. Arranged on the o-ring 15 is a first lid 7 for sealing the filling hole 14. The o-ring is arranged between the first lid 7 and the rigid top portion 4. The first lid 7 is pivotally connected to the rigid top portion 4. In the first lid 7 there is arranged a through-hole 16. The through-hole 16 is arranged such that a pressure valve 8 may be arranged in the though-hole 16. The pressure valve 8 may be arranged for maintaining a pressure of e.g. 150 mbar with 1500 ml of liquid at a temperature of 45° C. in the container 1. A second lid 9 is arranged to cover the pressure valve 8. For convenience, there is a handle 6 arranged at the top portion 4. A flexible tube 5 is arranged inside the compartment 17 formed by the side wall member 2 and the top 4 and bottom portions 3. At the bottom portion 3, there is a snap-in connection 18 for connecting a first end portion 19 of the flexible tube 5 to the bottom portion 3. A second end portion of the tube 5 is connected at the first hole 12 of the top portion 4 inside the compartment.

The lid 7 is preferably arranged to be maintained in a closed position, e.g. by means of a snap-lock arrangement or the like. For example, a hook or the like may be arranged on the inner side of the lid, to engage with an indentation, hole or the like on the outer wall of the upper top portion 4. Other type of locking arrangements are however also feasible. Further, the lid is preferably arranged to stay in an opened position when being opened. This may e.g. be accomplished by having non-planar surfaces in the hinge, a further snap-lock arrangement, or the like.

Figure 2:
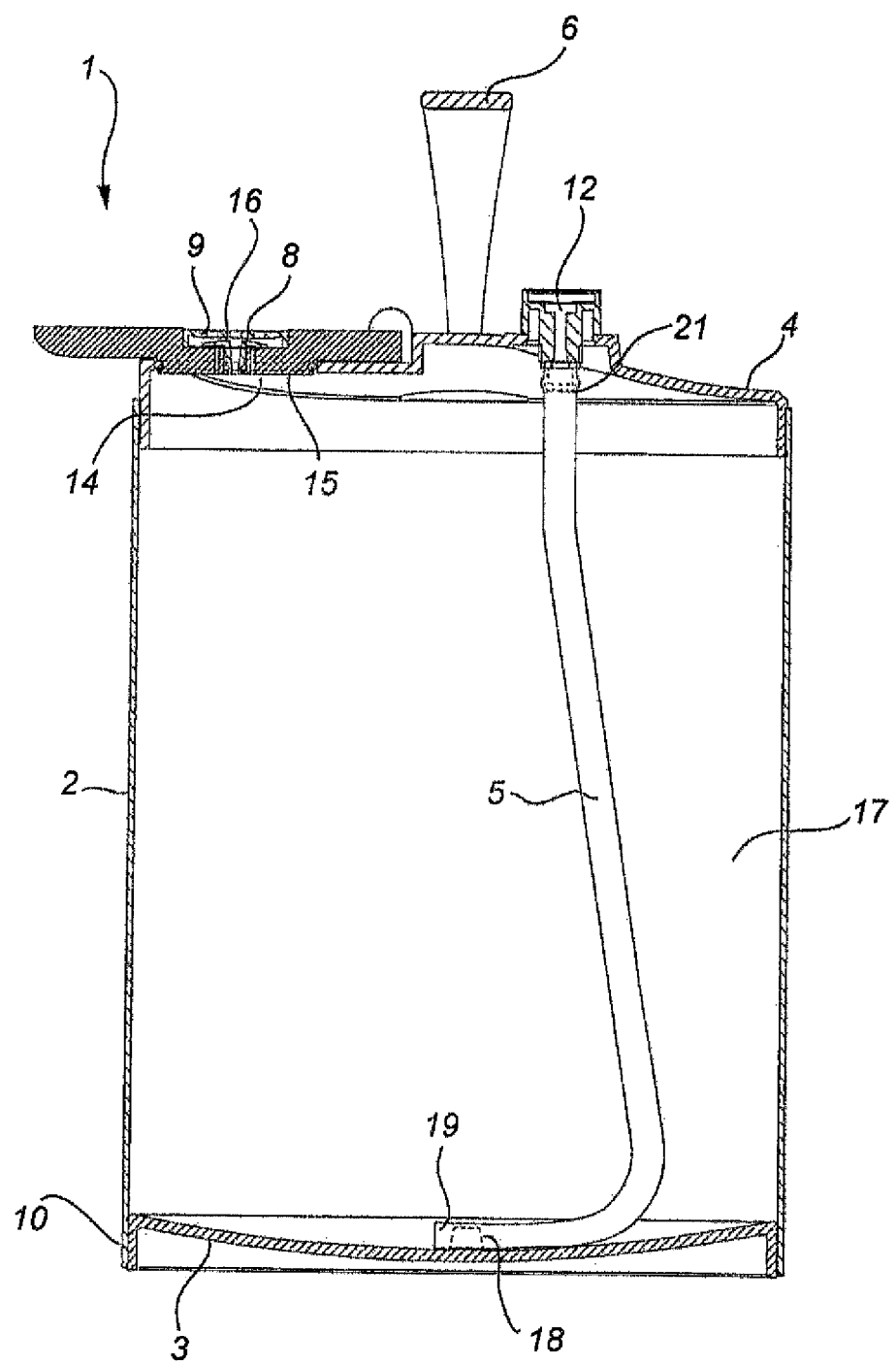
FIG. 2 is a cross-sectional view of the embodiment illustrated in FIG. 1.

The lid 7 is further preferably arranged to extend outside the edge of the upper top portion, as best seen in FIG. 2. Hereby, the opening procedure is facilitated, and opening can e.g. be effected by using the side of the hand, an edge of a table, sink or the like. Thus, opening is made simple also for users with reduced dexterity.

The side wall 2 is made from a flexible sheet material. The material may be a plastic material such as polypropylene, polyimide, polyethylene, EBA, or combinations thereof. The side wall member 2 of the illustrated embodiment is cylindrical in the expanded state. The flexible tube 5 may be made from silicone. The flexible tube 5 may further be twisted such that if the container 1 is in a collapsed state, as illustrated in FIG. 3b, the flexible tube 5 is curled up. A second through-hole is arranged in the top portion 4. Pressurized air may be supplied through the second hole 13 for pressurizing the compartment 17 when in use. In one embodiment, a temperature sensor is arranged on the side wall member 2. Further aspects of the container 1 will now be described with reference to FIG. 2.

FIG. 2 illustrates a cross-section of the container 1 in FIG. 1 with the cross-section taken along A-A'. In FIG. 2 the cross-section is taken of the container 1 when assembled. In FIG. 2, it is visible a container 1 which comprises a side wall member 2, a rigid bottom portion 3, a rigid top portion 4, a flexible tube 5, a handle 6, a first lid 7, a pressure valve 8, and a second lid 9. In this configuration, the flexible tube 5 is connected at a first end portion 19 to the bottom portion 3 at the snap-in connection. The flexible tube 5 is connected at a second end portion 21 to the top portion 4 at the first hole 12 and is in fluid connection with the first hole 12 such that fluid may flow though the tube 5 and through the first hole 12. The container 1 is configured such that if the compartment is pressurized, for example by inserting pressurized air through an opening or by pressurizing the compartment by any other means, a liquid stored in the compartment will flow through the flexible tube 5 through the first hole 12. The flexible tube 5 is connected at the bottom portion 3 which may facilitate emptying the container 1 when in use. The rigid bottom portion 3 enables a stable up-right position of the container 1.

The flexible side wall is preferably made of transparent or semi-transparent material. The side wall may further be provided with markings indicating a volume scale, relatable to the surface level of the liquid within the container. Hereby, it is possible to determine the volume that has been filled, the volume that has been pumped during use, etc. The scale may be arranged from the bottom with upwardly increasing numbers, or from the top, with downwardly increasing numbers. Since the container preferably has a uniform cross-sectional shape in the height direction, the scale may be linear.

The flexible side wall is preferably connected around the outer sides of the top and bottom portions, and may be connected by welding, adhesion, shrink fitting, etc, or a combination of these.

When the container is filled, and also when the container is pumped by pumping air into the container, the container will be relatively stable even though a very flexible material is used in the side wall. However, it is preferred to use a flexible material which has some degree of form stability.

The rigid top portion is preferably provided with an outwardly protruding, upwardly convex shape. Such a shape makes the top portion more rigid and stable.

The rigid bottom portion is preferably also provided with an outwardly protruding, downwardly concave shape. Hereby, the bottom of the container is interiorly bowl-shaped, having the lowest part at, or in the vicinity of, the center of the bottom portion, where the snap-in connection 18 for connecting a first end portion 19 of the flexible tube 5 is arranged. This ensures that very efficient drainage is made possible, allowing the container to be almost completely emptied, without any risk of pumping air instead of liquid. On the outside of bottom portion, a flat bottom area may be provided, or alternatively, as is shown in e.g. FIG. 2, an outer, and downwardly protruding rim may be provided, to ensure that the container is stable when standing on e.g. the floor.

Collapsing of the container 1 will now be described with reference to FIG. 3A and FIG. 3B where different states of the collapsible container 1 are illustrated.

Figure 3A:
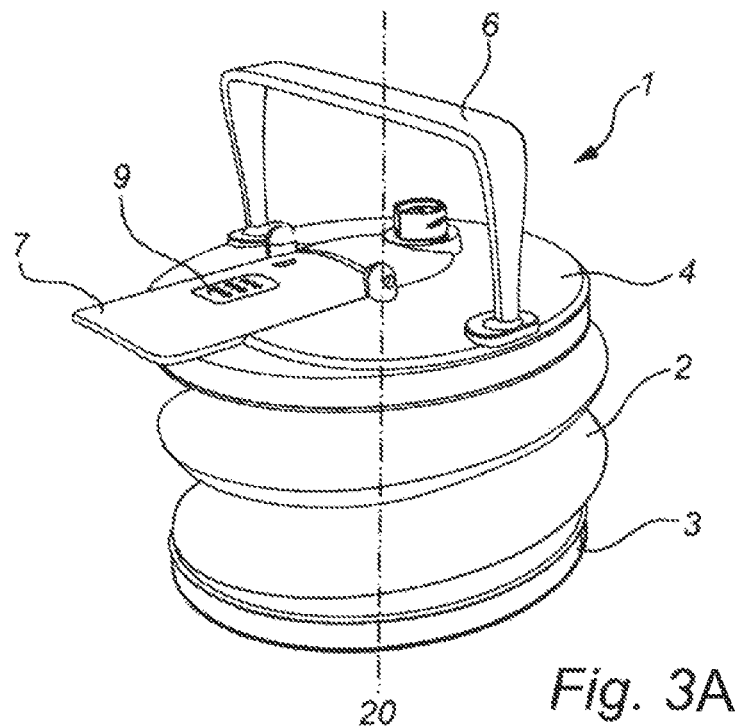
FIG. 3A is an illustration of a container according to the embodiment of FIGS. 1 and 2 in a partly collapsed state.
Figure 3B:
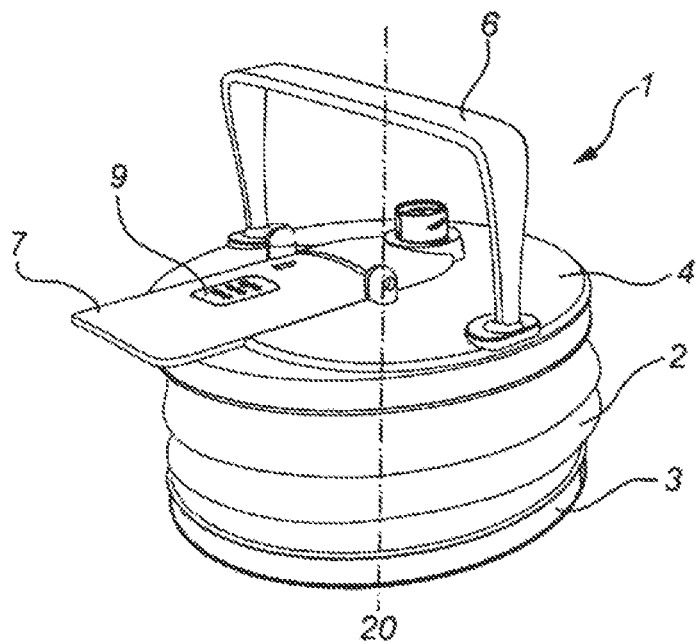
FIG. 3B is an illustration of a container according to the embodiment of FIGS. 1 and 2 in a collapsed state.

The illustrated embodiment in FIG. 2 illustrates the container in an expanded state, whereas FIGS. 3A and 3B illustrates the same container in a partly collapsed state and a collapsed state, respectively. In FIG. 3B, the container 1 has been collapsed along a longitudinal axis 20 of the container 1. In this state, the top portion 4 and the bottom portion 3 are relatively closer to each other as compared to in the partly collapsed state shown in FIG. 3A. The flexible tube 5 is twisted such that if the container 1 is in the collapsed state the flexible tube 5 is curled up. In one embodiment the top portion 4 is relatively rotated with respect to the bottom portion 3 in the expanded state as compared to in the collapsed state. The rotation is in a plane essentially perpendicular to the longitudinal axis of the container 1. A height of the container 1 in the collapsed state, from the top portion 4 to the bottom portion 3, is less than ½ the height of the expanded state, and preferably less than ⅓, and more preferably less than ¼, and even more preferred less than ⅕. In various embodiments, an element, for example a pivotally connected snap-in connection, is arranged to maintain the container 1 in the collapsed state. In an embodiment, the top 4 and bottom portion 3 are in contact with each other in a collapsed state.

Figure 4A:
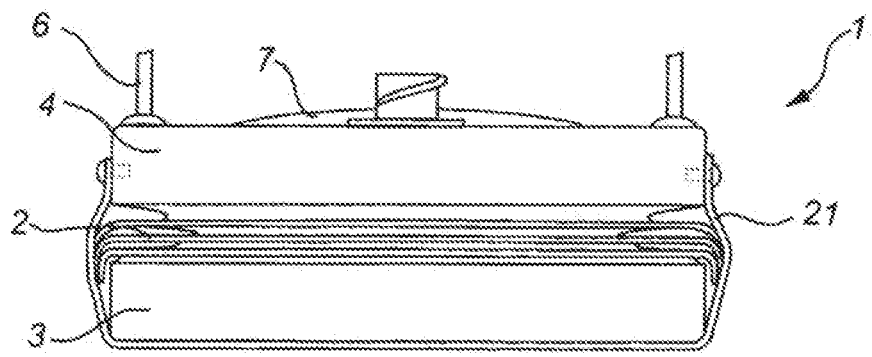
FIG. 4A is an illustration of the container of FIGS. 1 and 2 in an even more collapsed state, and having a first locking means for retaining the container in this collapsed state.
Figure 4B:
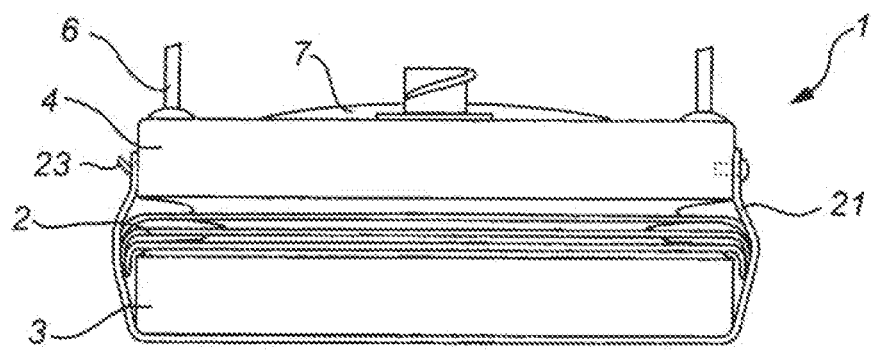
FIG. 4B is an illustration of the container of FIGS. 1 and 2 in an even more collapsed state, and having a second locking means for retaining the container in this collapsed state.
Figure 4C:
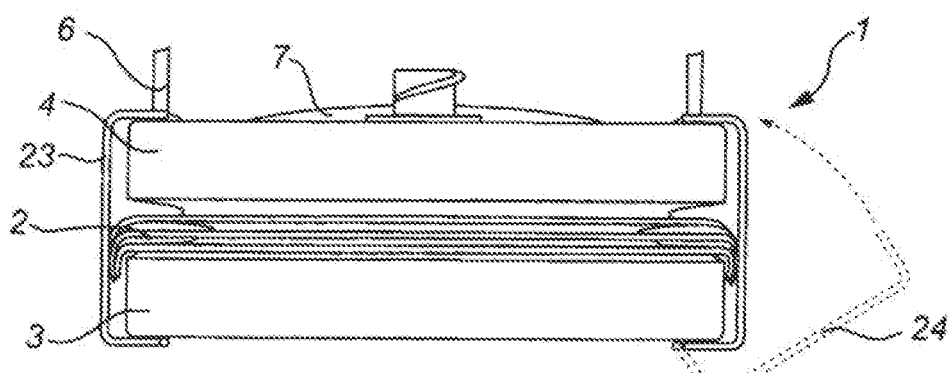
FIG. 4C is an illustration of the container of FIGS. 1 and 2 in an even more collapsed state, and having a third locking means for retaining the container in this collapsed state.

In FIG. 4, an even more collapsed state is illustrated. Here, the height of the collapsed container essentially corresponds to the heights of the top and bottom portions. In FIG. 4A, the collapsed container is retained in this state by means of locking means formed as a band 21, which is attached to one of the top and bottom portions, and which may be reversibly wrapped around the opposite portion. The band may be made of an elastic, stretchable material, but other materials are also useable. The band may also function as, or replace one of the above-discussed handles. In FIG. 4A, the band is fixedly connected at both ends. However, alternatively, the band may be releasably connected at one end, as is schematically illustrated in FIG. 4B. Here, a hook 22 or the like is provided, on which a hole in the band 21 may be fixed when in the connected disposition. An alternative locking arrangement is illustrated in FIG. 4C. Here, the locking means comprises locking fingers or hooks 23, being pivotably connected to one of the portions, and which may be pivoted into a locked state around the opposite portion.

Figure 5:
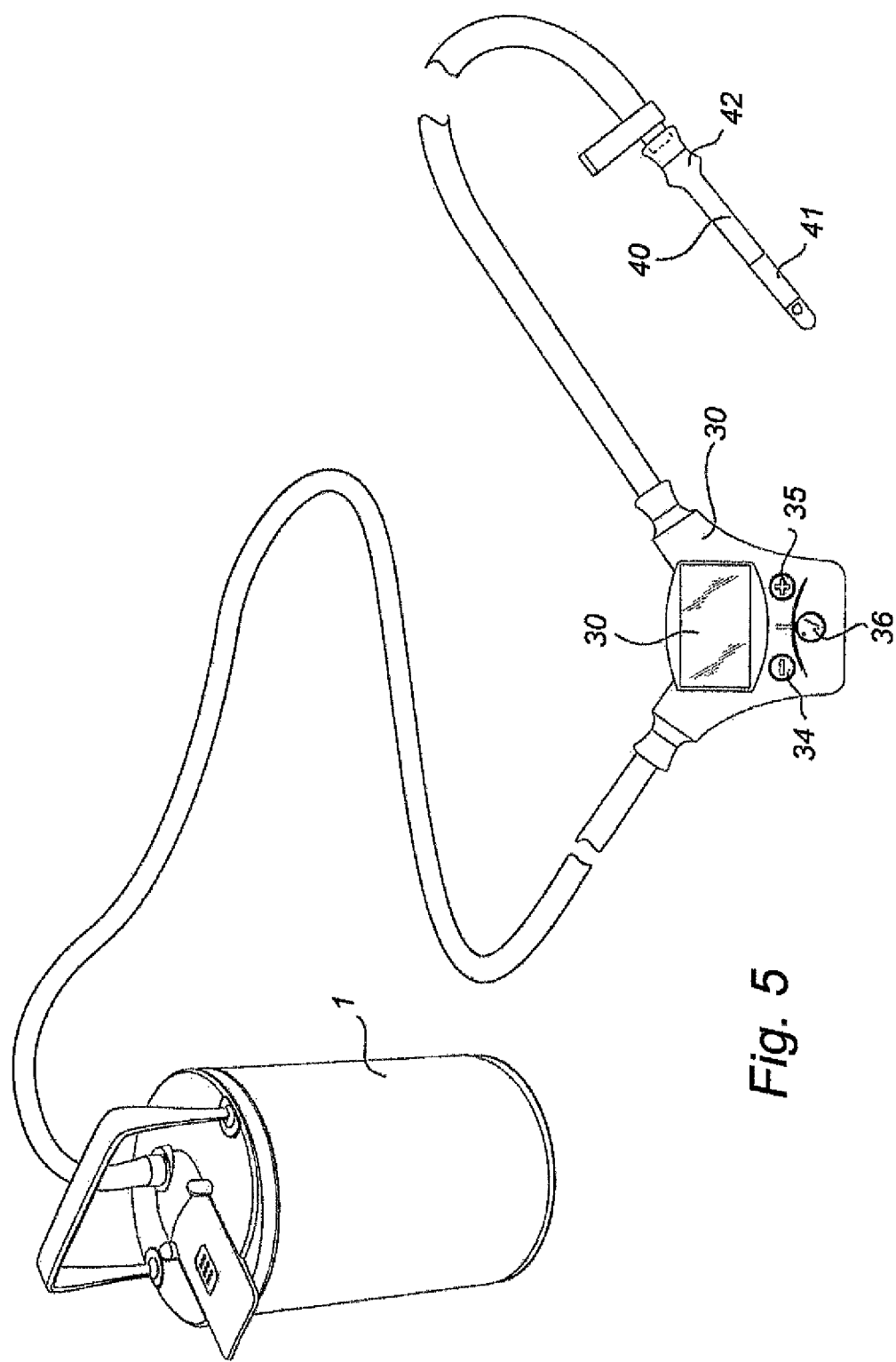
FIG. 5 is a schematic illustration of an irrigation system in accordance with an embodiment of the present invention, and comprising a collapsible container as illustrated in the preceding figures.

The above-discussed collapsible container is particularly useful as a reservoir in an irrigation system. Such an irrigation system, which is schematically illustrated in FIG. 5, typically comprises a reservoir, formed by the collapsible container 1, and arranged to house an irrigation liquid, a probe 20 for arrangement in a user, and a control unit 30.

Tubing connecting the reservoir to the rest of the irrigation system may be provided through the openings in the top portion of the collapsible container, but additional openings may also be provided.

In order to render the irrigation system as portable as possible, the container preferably has a capacity of less than 5 liters, more preferred less than 3 liters and most preferred less than 2 liters. If however the system is to be used for repeated irrigation, a larger capacity container may be necessary.

As discussed previously, the container preferably comprises an overpressure release valve, to release pressure over a predetermined maximum pressure to be allowed. Further, the reservoir preferably comprises a filter, such as a hydrophobic filter, which is impermeable to the irrigation liquid, but which allows air to enter the reservoir but not escape the reservoir. Such a filter ensures that the reservoir maintains its shape when irrigation liquid is being pumped out from the reservoir. This is of advantage, since it makes the reservoir more stable. It also makes it possible to use less costly materials and less rigid containers when producing the reservoir, thereby making the production more cost-efficient. This ensures that the reservoir remains stable during irrigation. However, alternative means for obtaining this are also feasible. For example, the reservoir may simply be provided with an air inlet, possibly provided with a back-valve to prevent outflow of irrigation liquid, should the irrigation liquid reach the inlet.

For pumping, one or several manual and/or electric pump(s) may be used. The pump(s) may be arranged to pump liquid from the container directly, or to pump air or any other gas into the container to provide an overpressure which effects pumping, in the above-discussed manner.

The probe 40 is preferably provided with a retention member, such as an inflatable balloon 41, for fixing the catheter in a body cavity. Further, the probe may be provided with a rearward enlarged part 42, providing an abutment to hinder too deep insertion. The probe is provided with two lumens—one lumen for transfer of irrigation liquid through the probe, for discharge at the forward end, and one lumen for inflation and deflation of the balloon.

The control unit may be realized as a unitary, hand-held unit. The control unit may comprise a display 33, and one or several control elements 34, 35 and 36.

Tubing is arranged to connect the reservoir, control unit and probe together. Preferred materials for the bulb pumps and the balloon can be any suitable material e.g. such as PVC, latex, TPE or PU. However, other materials providing similar properties can likewise be used.

The irrigation liquid can be any liquid which is capable of irrigation the body cavity of interest. In order to stimulate bowel movements suitable irrigation liquids includes water, hypertonic aqueous salt solutions, solutions or suspensions of cathartic agents, such as bisacodyl or phenolphthalein, and mineral oil.

The person skilled in the art realizes that the present invention is not limited to the preferred embodiment. For example, the side wall member may be of a different shape than the described cylindrical shape. It may for example have a polygonal shape in a cross-section comprising a circumference of the side wall member. Furthermore, the pressure, volume and temperature of the liquid in the container are not limited to what is described in the embodiments, but are merely an example. Materials mentioned are examples and are not limiting the invention. Further, the collapsible container is particularly suitable for use as a reservoir for housing irrigation liquid for use in an irrigation system for rectal or urethral irrigation. However, the collapsible container may also be used in many other types of medical procedures and systems. Further, the collapsible container may be arranged so that the liquid is pumped directly from the container, or indirectly, by providing a pressure inside the container. The container may also be used for receiving liquid during a medical procedure.

Such and other obvious modifications must be considered to be within the scope of the present invention, as it is defined by the appended claims. It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting to the claim. The word "comprising" does not exclude the presence of other elements or steps than those listed in the claim. The word "a" or "an" preceding an element does not exclude the presence of a plurality of such elements. Further, a single unit may perform the functions of several means recited in the claims.

The invention claimed is:

1. A container (1) for medical use forming a closed compartment (17) for carrying a liquid, comprising:
    a side wall member (2) formed by a sheet material and forming a side wall of said closed compartment (17), said side wall member (2) comprising oppositely arranged first (10) and second (11) open ends;
    a rigid bottom portion (3) arranged at said first open end (10) of said side wall member (2) such that said bottom portion (3) seals said first open end (10) of said side wall member (2), thereby forming a bottom of said closed compartment (17);
    a rigid top portion (4) arranged at said second open end (11) of said side wall member (2) such that said top portion (4) seals said second open end (11) of said side wall member (2), said top portion (4) forming the top of said container (1), and having a first through going hole and a lid (7) pivotably connected to said top portion (4) and arranged to cover and seal a filling hole (14), wherein said lid (7) arranged on said top portion (4) comprises a pressure valve (8) arranged and configured to hold a pressure of at least 150 mbar inside said container (1); and
    a flexible tube (5) arranged inside said compartment (17), said tube (5) having a first end portion (19) and a second end portion (21);
    wherein, said first end portion (19) of said tube (5) is connected to said bottom portion (3), said first end portion (19) being provided with an opening towards said compartment (17), and said second end portion (21) is connected to said top portion (4) and in fluid communication with said first hole (12) of the rigid top portion (4);
    wherein said side wall member (2) is flexible such that said container (1) is reversibly foldable and unfoldable, thereby being arrangeable in a compact state, in which the rigid top and bottom (3) portions are arranged relatively closer to each other, and in an expanded state, in which the rigid top and bottom (3) portions are arranged relatively further apart, respectively.

2. The container (1) according to claim 1, wherein a second through going hole (13) is arranged such that, when in use, liquid may pass through said tube (5) and said first hole (12) through a sealed connection between said tube (5) and said top portion (4), and such that if pressurized gas is supplied through said second hole (13), when in use, liquid from inside said compartment (17) will be provided through said tube (5) and through said first hole (12).

3. The container (1) according to claim 1, wherein said flexible tube (5) is twisted, to curl up when said container (1) is brought to said compact state.

4. The container (1) according to claim 1, further comprising at least one locking element to maintain said container (1) in said compact state.

5. The container (1) according to claim 1, further comprising at least one handle (6) in said top portion (4) and/or in said bottom portion.

6. The container (1) according to claim 1, wherein in said compact state, said top (4) and bottom portions (3) are in contact with each other.

7. The container (1) according to claim 1, wherein in said compact state, said top (4) and bottom portions (3) are rotated relative each other compared to when in said expanded state.

8. The container (1) according to claim 1, wherein in said compact state, said container (1) is less than ½ the height of the expanded state.

9. The container (1) according to claim 1, wherein said side wall member (2) is cylindrical in the expanded state.

10. The container (1) according to claim 1, wherein said container (1) is adapted for use in an irrigation system.

11. The container (1) according to claim 1, wherein said tube (5) is attached to said bottom portion (3) via a snap-in connection (18).

12. An irrigation system, comprising a container in accordance with claim 1.

* * * * *